(12) United States Patent
Pesce et al.

(10) Patent No.: US 6,833,487 B2
(45) Date of Patent: Dec. 21, 2004

(54) ARTICLES COMPRISING A CATIONIC POLYSACCHARIDE AND SILICA

(75) Inventors: Antonella Pesce, Pescara (IT); Adelia Alessandra Tordone, Pescara (IT); Giovanni Carlucci, Chieti (IT); Achille Di Cintio, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 190 days.

(21) Appl. No.: 10/241,891

(22) Filed: Sep. 12, 2002

(65) Prior Publication Data

US 2003/0022574 A1 Jan. 30, 2003

Related U.S. Application Data

(63) Continuation of application No. PCT/US01/13160, filed on Apr. 24, 2001.

(30) Foreign Application Priority Data

Apr. 25, 2000 (EP) ............................................. 00108065

(51) Int. Cl.[7] .......................... B32B 27/04; B32B 27/12; A61F 13/15
(52) U.S. Cl. .......................... 604/358; 442/121; 442/96; 604/359
(58) Field of Search ................................. 604/364, 359, 604/304, 374, 375, 385.101, 385.01, 358; 442/121, 96; 424/76.1, 76.4; 428/113, 101, 109

(56) References Cited

U.S. PATENT DOCUMENTS

| 5,211,870 | A | * | 5/1993 | Gilbert et al. .............. 510/153 |
| 5,599,916 | A | * | 2/1997 | Dutkiewicz et al. .......... 536/20 |
| 5,650,384 | A | * | 7/1997 | Gordon et al. ............... 510/159 |
| 5,932,495 | A |   | 8/1999 | Boney |
| 2003/0018312 | A1 | * | 1/2003 | Pesce et al. ................. 604/375 |
| 2003/0022573 | A1 | * | 1/2003 | Cintio et al. .................. 442/96 |
| 2003/0023216 | A1 | * | 1/2003 | Carlucci et al. ............. 604/375 |
| 2003/0049480 | A1 | * | 3/2003 | Gagliardini et al. ......... 428/532 |
| 2003/0232895 | A1 | * | 12/2003 | Omidian et al. ............... 521/99 |
| 2004/0170589 | A1 | * | 9/2004 | Gatto ....................... 424/70.13 |

FOREIGN PATENT DOCUMENTS

| EP | 0 811 392 A1 | 12/1997 |
| GB | 2 292 526 A | 2/1996 |
| WO | WO 91/12029 A1 | 8/1991 |
| WO | WO 99/32697 A2 | 7/1999 |
| WO | WO 99/55393 A1 | 11/1999 |

* cited by examiner

*Primary Examiner*—Cheryl A. Juska
*Assistant Examiner*—Lynda Salvatore
(74) *Attorney, Agent, or Firm*—Bridget D. Ammons; Kevin C. Johnson

(57) ABSTRACT

The present invention relates to articles, preferably disposable absorbent articles like sanitary napkins and pantiliners, which comprise a cationic polysaccharide, preferably chitosan material, and silica. Such disposable absorbent articles deliver improved odor control performance (synergistic odor reduction) and improved fluid handling properties/absorption performance. In one embodiment of the present invention, articles are provided which comprise crosslinked silica-cationic polysaccharides. These articles deliver not only improved odor control and fluid handling properties when in use but are able to maintain these properties even upon prolonged wearing time, typically upon ageing of the bodily fluid in the articles and/or upon subsequent fluid discharge in the articles.

15 Claims, No Drawings

ARTICLES COMPRISING A CATIONIC POLYSACCHARIDE AND SILICA

CROSS REFERENCE TO RELATED REFERENCES

This is a continuation of International Application PCT/US01/13160 with an International filing date of Apr. 24, 2001.

FIELD OF THE INVENTION

This invention relates to articles, such as disposable absorbent articles, comprising a cationic polysaccharide, preferably chitosan material, together with silica.

BACKGROUND OF THE INVENTION

Malodors may be present in the environment from numerous sources both animate and inanimate. Many products and articles are available which aim to avoid or minimize the detection of such odors. In particular, it is particularly desirable to provide odor control materials to address the malodors which are generated by the human body, or from bodily fluids such as perspiration, urine, faeces, menstrual fluids, vaginal fluids and the like.

Articles like absorbent articles for example are designed to be worn by humans to absorb bodily fluids, such as urine, menstrual fluid and perspiration, etc. Examples of absorbent articles include sanitary napkins, pantiliners, disposable diapers, incontinence pads, tampons, perspiration pads, nursing pads and the like.

In use, the absorbent articles are known to acquire a variety of compounds, for example volatile fatty acids (e.g. isovaleric acid), ammonia, amines (e.g. triethylamine), sulphur containing compounds (e.g. mercaptans, sulphides), alcohols, ketones and aldehydes (e.g., furaldehyde) which release unpleasant odors. These compounds may be present in the bodily fluid or may be developed by chemical reactions and/or any fluid degradation mechanisms once the bodily fluid is absorbed into the absorbent article like for example a feminine pad. In addition bodily fluids usually contain micro-organisms and/or enzymes that can also generate malodorous by products as a result of degradation mechanisms like putrefactive degradation, acid degradation, proteins degradation, fat degradation and the like. Unpleasant odors, which emanate from absorbent pads when in use, may make the wearer feel self-conscious.

Various odor control materials have been disclosed in the art to combat some of the unpleasant odors referred to above. Indeed solutions have been provided that use different technical approaches like masking, i.e., covering the odor with a perfume, or absorbing the odor already present in the bodily fluids and those generated after degradation or preventing the formation of the odor.

Most of the focus in the prior art is found on the odor absorption technology. Examples of these types of compounds include activated carbons, clays, zeolites, silicas, starches, cyclodextrine, ion exchange resins and various mixture thereof as for example described in EP-A-348 978, EP-A-510 619, WO 91/12029, WO 91/11977, WO 89/02698, and/or WO 91/12030. All of these types of odor controlling agents are believed to control odor by mechanisms whereby the malodorous compounds and their precursors are physically absorbed by the agents and thus such agents hinder the exit of the odor from articles like absorbent articles. However, such mechanisms are not completely effective as the formation of the odor itself is not prevented and thus odor detection is not completely avoided. Some of the focus in the prior art has also been on the use of antimicrobial agents, amongst which chitosan and chitin based materials have been listed. For example WO 99/32697 discloses that chitosan and chitin-based polymers exhibit increased antimicrobial activity when coated onto the surface of a hydrophobic material such as polypropylene.

Although these materials provide some control of odors associated with bodily fluids, there still exists a need of further improvement in terms of odor control over a wide range of malodorous compounds.

There is ongoing work in this direction as illustrated in WO 99/61079. For example WO 99/61079 discloses odor reduction for products such as disposable diapers and training pants, sanitary napkins and tampons by the use of triglycerides and polyglycosides to enhance the malodor absorption properties of compositions and substrates such as naturally occurring polymers like chitosan or alginates and synthetic polymers treated with surfactants.

But there is still a need for further solutions to improve odor control performance of articles like disposable absorbent articles, beside the primary focus of such articles, which remain the ability of such articles to absorb and retain fluid.

Accordingly it is an object of the present invention to provide articles, especially disposable absorbent articles, which deliver outstanding odor control over a broad spectrum of malodors. More particularly it is an object to provide this benefit without impairing on the fluid handling properties of such articles, like fluid absorption and fluid retention.

It has now been found that the above needs can be addressed by combining a cationic polysaccharide together with silica, as the odor control system for an article, preferably a disposable absorbent article.

It has surprisingly been found that the combination of silica and a cationic polysaccharide, preferably chitosan material, in an article, like an absorbent article, typically coming into contact with bodily fluids, results in a synergistic effect in terms of odor control. Indeed this combination gives more odor reduction than the odor reduction associated with the use of one of these two classes of ingredients alone at the same total level (either silica alone or the cationic polysaccharide alone) in an absorbent article contacted with bodily fluids. Furthermore it has been found that the addition of silica to a cationic polysaccharide like chitosan material also improves the fluid handling properties of chitosan material. Indeed the articles of the present invention, typically the disposable absorbent articles comprising silica on top of the cationic polysaccharide, namely chitosan material, deliver improved fluid absorption and fluid retention as compared to the same articles without any silica.

Actually the combination of a cationic polysaccharide with silica in an article herein allows combining odor control mechanisms by which the overall malodor detection is synergistically reduced or even prevented.

Without to be bound by any theory it is believed that cationic polysaccharides, preferably chitosan materials, provide odor control of malodorous components associated with bodily fluid by multiple mechanisms.

Firstly, the odor absorption and retention characteristics of polysaccharides are due to the presence in the polymer structure of ionisable cationic functional groups. These groups are usually ammonium groups, a high proportion of which are in the salt form when the polymer is dry but which undergo dissociation and salvation upon contact with bodily fluid. In the dissociated state, the polymer chain will have a series of functional groups attached to it which groups have the same electric charge (e.g., —$NH_3^+$ $^+H_3N$—) and thus repel one another. This leads to expansion of the polymer structure, which, in turn permits further absorption of negatively charged odorous molecules. Importantly the odor absorption property of cationic polysaccharides, especially chitosan materials, is not linked to the particle size of the absorbed odorous molecules but to their electrostatic properties.

Secondly, the positively charged cationic groups of the polysaccharides will interact with negatively charged anionic functionalities present in bodily fluids, like the carboxylic groups of proteins or hydroxylic acid bearing entities like short chain acid (e.g., butyric acid). This will result in the formation of tri-dimensional net between cationic polysaccharides and such molecules with anionic groups (gelification of the bodily fluids). This gelification will entrap most odorous molecules (like lipids, acids) thereby controlling malodor.

Thirdly and more importantly the cationic polysaccharides especially the aminopolysaccharides (preferably the chitosan materials) are believed to act as antimicrobial agents. Indeed the polysaccharides with their positively charged cationic groups will interfere with negatively charged surface of microorganism walls, thereby inhibiting the growth of such microorganisms or even killing such microorganisms. These cationic polysaccharides will also interfere with negatively charged surface of enzymes, thereby inactivating the enzymatic activity, which, like the microbial activity, are otherwise responsible for the formation of malodorous components. The cationic polysaccharides like chitosan materials further act by their indirect antimicrobial activity by linking some of the microorganism nutriments like lipids and/or minerals.

Advantageously the presence of silica boosts the odor controlling properties of the cationic polysaccharides, namely chitosan materials. Indeed the presence of silica increases the cationic properties of the cationic polysaccharides, typically chitosan materials, which result in enhanced antimicrobial activity, enhanced odor absorption and enhanced gelification properties. Without to be bound by any theory it is believed that the acidic properties of silica (silica materials have a pH between 3 and 5) protonate the amino groups of the cationic polysaccharides like chitosan materials, enhancing thereby the numbers of positively charged ammonium groups (—$NH_3^+$) of the chitosan materials and thus the cationic character of the chitosan materials.

Advantageously the presence of the cationic polysaccharides, like chitosan materials, increases the odor absorption effectiveness of silica. Silica is an odor absorbent material per se. It is especially effective towards amino containing compounds like trimethylamine, urea. Without to be bound by any theory it is speculated that the cationic polysaccharides herein, typically chitosan materials, control the enzymatic and microbial growth and as a consequence the amount of malodorous compounds associated with the enzymatic and microbial activity occurring in bodily fluid. In other words, the cationic polysaccharides reduce or even prevent the formation of malodorous compounds, thereby reducing the total amount of malodor to be controlled. This allows silica to work in reduced amount of active. Actually this results in a more effective as well as a sustained use of silica as odor absorbent material. Indeed the saturation point of silica when used in association with a cationic polysaccharide will be reached after prolonged periods of use, typically after prolonged wearing time of an absorbent article (e.g., pantiliner, pad) coming into contact with bodily fluid, as compared to when used alone in absence of the cationic polysaccharide in the same conditions. Advantageously it is believed that silica also helps the cationic polysaccharides in reducing malodor by adsorbing the odor of head space (space between the absorbent article and the urogenital surface) and accordingly volatile malodorous components, which escape from the bodily fluid and hence will not be in direct contact with the cationic polysaccharides.

The use of cationic polysaccharides like chitosan materials together with silica in absorbent articles also provides improved body fluid absorbing and retention performance. Indeed silica enhances the conversion of the cationic polysaccharides, especially chitosan materials, in the corresponding salt forms increasing thereby their capacity of absorbing fluid and forming three-dimensional network with anionic molecules present in the fluids (like proteins, lipid and so on).

In an embodiment of the present invention the articles comprise crosslinked silica-cationic polysaccharides, preferably crosslinked silica-chitosan. Preferably the crosslinking agent used is an agent being able to also deliver some odor controlling benefits per se. Highly preferred crosslinking agents for use herein are multi-basic acids like citric acid. It has now been observed that by using crosslinked silica-cationic polysaccharides, especially crosslinked silica-chitosan, long lasting odor control properties are delivered, especially long lasting antimicrobial benefits.

In a crosslinked silica-cationic polysaccharide, the crosslinking agent binds both the cationic polysaccharide and the silica, by electrostatic interaction or covalent bonding (e.g., esterification). Without to be bound by any theory it is speculated that this crosslinking results in insolubilization of the cationic polysaccharide, like chitosan material, and hence in reduced washability of such material when submitted to subsequent bodily fluid discharge. Furthermore upon contact with bodily fluid a slow dissociation will occur resulting in slow and hence sustained release of silica, chitosan material and crosslinking agent. This slow dissociation releases odor control actives in time sequence with bodily fluid discharge in an absorbent article and hence delivers long lasting odor control activity.

In a preferred embodiment herein the disposable absorbent articles have an apertured polymeric film topsheet. This topsheet contributes to further improve the odor control benefit.

In another preferred embodiment herein the disposable absorbent articles have a breathable backsheet. This contributes to a further improved odor control benefit. Even more preferred herein the disposable absorbent articles have both a breathable backsheet and an apertured polymeric film topsheet.

The present invention is preferably directed to disposable absorbent articles like pantiliners, feminine napkins, incontinent pads, diapers, tampons, interlabial pads, perspiration pads, surgical pads, breast pads, human or animal waste management devices and the like. Other articles suitable for use according to the present invention further include articles designed to be placed against or in proximity to the body such as clothing, bandages, thermal pads, acne pads, cold pads, compresses, surgical pads/dressings and the like, body cleansing articles like impregnated wipes/tissues (e.g. baby wipes, wipes for feminine intimate hygiene), articles for absorbing perspiration such as shoe insoles, shirt inserts, and the like, and articles for animals like litters and the like.

SUMMARY OF THE INVENTION

This invention relates to articles, such as disposable absorbent articles, comprising a cationic polysaccharide together with silica.

The present invention also encompasses a method of controlling odor associated with bodily exudates and/or bodily fluids, wherein said bodily exudates and/or fluids are contacted with an odor control system comprising a cationic polysaccharide, preferably chitosan material, together with silica as well as the use of a crosslinked silica-cationic polysaccharide, preferably a crosslinked silica-chitosan material, in an absorbent article suitable to be placed against or in proximity to the body of a wearer, to deliver improved odor control and/or long lasting odor control.

DETAILED DESCRIPTION OF THE INVENTION

By "article" it is meant herein any three-dimensional solid material being able to comprise a cationic polysaccharide and silica. The term "disposable" is used herein to describe articles, which are not intended to be launched or otherwise restored or reused as an article (i.e., they are intended to be discarded after a single use and, preferably to be recycled, composted or otherwise disposed of in an environmentally compatible manner). The term "absorbent article" is used herein in a very broad sense including any article able to receive and/or absorb and/or contain and/or retain fluids and/or exudates, especially bodily fluids/bodily exudates.

Preferred articles according to the present invention are disposable absorbent articles that are designed to be worn in contact with the body of a user and to receive fluids/exudates discharged from the body, such as pantiliners, sanitary napkins, catamenials, incontinence inserts/pads, diapers, tampons, interlabial pads/inserts, breast pads, human or animal waste management devices and the like. Typically such human urine or faecal management devices comprise a bag having an aperture and a flange surrounding the aperture for preferably adhesive attachment to the urogenital area and/or the perianal area of a wearer. Any faecal or urine management device known in the art is suitable for use herein. Such devices are described in for example WO 99/00084 to WO 99/00092. Other suitable articles according to the present invention also include other articles designed to be placed against or in proximity to the body such as clothing, bandages, thermal pads, acne pads, cold pads, compresses, surgical pads/dressings and the like, articles for absorbing perspiration such as shoe insoles, shirt inserts, perspiration pads and the like, body cleansing articles like impregnated wipes/tissues (e.g. baby wipes, wipes for feminine intimate hygiene), and the like, and articles for animals like litters and the like.

By "bodily fluids and/or bodily exudates" it is meant herein any fluid/exudate produced by human or animal body occurring naturally or accidentally like for instance in the case of skin cutting, including for instance perspiration, urine, menstrual fluids, faeces, vaginal secretions and the like.

Silica

According to the present invention the articles comprise as an essential component silica.

Silica, i.e. silicon dioxide $SiO_2$ exists in a variety of crystalline forms and amorphous modifications, any of which are suitable for use herein. In particular, silicas having a high surface area or in agglomerated form are preferred. Silica molecular sieves are not considered to be within the definition of silica as used herein. Suitable silica for use herein may have a silica content, which is equivalent to 1% to 100% by weight of $SiO_2$.

Suitable silica for use herein is for instance Silica gel 123® or Syloblanc 82® available from Grace GmbH.

Silica for use according to the present invention also includes metal silicates, such as silicates of group Ia and group IIa metals, namely sodium silicate or potassium silicate.

According to the present invention the articles typically comprise from 5 to 300 $gm^2$, more preferably from 10 to 250 $gm^2$ most preferably from 15 to 200 $gm^2$, of silica based on 100% purity or a mixture thereof.

Without to be bound by any theory it is speculated that silica controls odor associated with bodily fluids/exudates not only by absorbing malodorous compounds, especially amino-containing compounds like trimethylamine and/or urea, present in the bodily fluids coming into contact therewith typically in the absorbent article, but also those present in the headspace.

Furthermore, silica acts as an odor-controlling agent due to its acidic properties (silicas typically have a pH between 3 and 5). Silica is usually capable of keeping the pH of the bodily fluid near neutrality, thereby controlling the formation of alkaline odorous components, like ammonia and amines, which are responsible of some unpleasant odors.

Advantageously silica due to its acidic character has the ability to protonate the amino groups of the cationic polysaccharides, enhancing thereby the numbers of positively charged ammonium groups ($-NH_3^+$) of the cationic polysaccharides and thus the cationic properties of the cationic polysaccharides. In other words, the presence of silica boosts the odor control properties of the cationic polysaccharide, namely chitosan material, resulting in a synergistic odor reduction towards odor associated with bodily fluid like menses as well as enhances the fluid handling properties of the cationic polysaccharides.

Cationic Polysaccharides

According to the present invention the articles comprise as an essential component a cationic polysaccharide or a mixture thereof.

Suitable cationic polysaccharides for use herein are positively charged polysaccharides due to the presence of cationic functional groups. Suitable polysaccharides for use herein include natural and semi-synthetic cationic polysaccharides. Examples of suitable cationic functional groups include primary, secondary or tertiary amine groups or quaternary ammonium groups, which should be present in base form. Preferably quaternary ammonium groups are present. Such cationic polysaccharides are also called herein amino polysaccharides. The cationic polysaccharides for use herein might be a fibrous polysaccharide such as cellulose with an excess of quaternary ammonium compound containing at least one group capable of reacting with polysaccharide hydroxyl groups. Such cationic polysaccharides are described in WO 92/17681, herein incorporated by reference. Highly preferred herein are aminopolysaccharides, namely chitin-based materials, chitosan materials and mixture thereof.

By 'chitosan material' it is meant herein chitosans, modified chitosans, and chitosan salts.

Chitosan is a partially or fully deacetylated form of chitin, a naturally occurring polysaccharide. Indeed, chitosan is an aminopolysaccharide usually prepared by deacetylation of chitin (poly-beta(1,4)-N-acetyl-D-glucosamine).

Chitin occurs widely in nature, for example, in the cell walls of fungi and the hard shell of insect and crustaceans. The waste from shrimp-, lobster-, and crab seafood industries typically contains about 10 to about 15 percent chitin and is a readily available source of supply. In the natural state, chitin generally occurs only in small flakes or short fibrous material, such as from the carapace or tendons of crustaceans. There is generally no source, as with cotton in the cellulosics, that forms useful shaped articles without solution and re-precipitation or re-naturing.

More specifically, chitin is a mucopolysaccharide, poly-N-acetyl-D-glucosamine with the following formula:

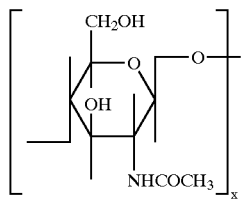

wherein x represents the degree of polymerization. Although x cannot be determined precisely, x is believed to be commonly in the range of from about 30 to about 50,000.

Chitosan is not a single, definite chemical entity but varies in composition depending on the conditions of manufacture. It may be equally defined as chitin sufficiently deacetylated to form soluble amine salts. Chitosan is the beta-(1-4) polysaccharide of D-glucosamine, and is structurally similar to cellulose, except that the C-2 hydroxyl group in cellulose is substituted with a primary amine group in chitosan. The large number of free amine groups makes chitosan a polymeric weak base. Solutions of chitosan are generally highly viscous, resembling those of natural gums.

The chitosan used herein is suitably in relatively pure form. Methods for the manufacture of pure chitosan are well known. Generally, chitin is milled into a powder and demineralized with an organic acid such as acetic acid. Proteins and lipids are then removed by treatment with a base, such as sodium hydroxide, followed by chitin deacetylation by treatment with concentrated base, such as 40 percent sodium hydroxide. The chitosan formed is washed with water until the desired pH is reached.

The properties of the aminopolyssaccharides, especially chitosan, relate to their polyelectrolyte and polymeric carbohydrate character. Thus, chitosan is generally insoluble in water, in alkaline solutions at pH levels above about 6.5, or in organic solvents. It generally dissolves readily in dilute solutions of organic acids such as formic, acetic, tartaric, glycolic, lactic and citric acids, and also in dilute mineral acids, except, for example, sulfuric acid. In general, the amount of acid required to dissolve chitosan is approximately stoichiometric with the amino groups. Since the pKa for the amino groups present in chitosan material is between 6.0 and 7.0, they can be protonated in very dilute acids or even close to neutral conditions, rendering a cationic nature to this biopolymer. This cationic nature is the basis of many of the benefits of the chitosan material. More generally, the cationic polysaccharides, like chitosan material, can be considered as a linear polyelectrolyte with a high charge density which can interact with negatively charged surfaces, like proteins (e.g., by interfering with the negatively charged wall construction of microorganisms and/or enzymes, thereby acting as an antimicrobial agent and/or by reacting with the proteins present in bodily fluid, like menses, thereby acting as a gelifying agent for such fluid) or like anionic absorbent gelling materials that might be present in the articles herein as an optional ingredient (e.g., in a preferred embodiment of the present invention, thereby further enhancing the odor control properties of the cationic polysaccharides and providing outstanding fluid absorption properties even in presence of electrolyte-containing solutions).

Preferred chitosan materials for use herein have an average degree of deacetylation (D.A.) of more than 75%, preferably from 80% to about 100%, even more preferably from 90% to 100% and most preferably from 95% to about 100%. The degree of deacetylation refers to the percentage of the amine groups that are deacetylated. This characteristic is directly related to the hydrogen bonding existing in this biopolymer, affecting its structure, solubility and ultimately its reactivity. The degree of deacethylation can be determined by titration, dye adsorption, UV-VIS, IR, and NMR spectroscopy.

The degree of deacetylation will influence the cationic properties of chitosan material. By increasing the degree of deacetylation the cationic character of chitosan materials will increase and thus their antimicrobial properties, absorbing ability and gelifying ability.

Chitosan materials may generally have a wide range of molecular weights. Chitosan materials with a wide range of molecular weights are suitable for use in the present invention, typically chitosan materials for use herein have a molecular weight ranging from 1,000 to 10,000,000 grams per gram moles and more preferably from 2,000 to 1,000,000. Molecular weight means weight average molecular weight. Methods for determining the weight average molecular weight of chitosan materials are known to those skilled in the art. Typical methods include for example light scattering, intrinsic viscosity and gel permeation chromatography. It is generally most convenient to express the molecular weight of a chitosan material in terms of its viscosity in a 1.0 weight percent aqueous solution at 25° C. with a Brookfield viscometer. It is common to indirectly measure the viscosity of the chitosan material by measuring the viscosity of a corresponding chitosan salt, such as by using a 1.0 weight percent acetic acid aqueous solution. Chitosan materials suitable for use in the present invention will suitably have a viscosity in a 1.0 weight percent aqueous solution at 25° C. of from about 1 mPa·s (1 centipoise) to about 80,000 mPa·s (80,000 centipoise), more suitably from about 30 mPa·s (30 centipoise) to about 10,000 mPa·s (10,000 centipoise), even more suitably from 50 mPa·s (50 centipoise) to about 1,000 mPa·s (1,000 centipoise) and most suitably from 100 mPa·s (100 centipoise) to about 500 mPa·s (500 centipoise).

Chitosan materials pH depends on the preparation of the chitosan materials. Preferred chitosan materials for use herein have an acidic pH, typically in the range of 4 to 6, more preferably from 4 to 5.5 and even more preferably from 4.5 to 5.5. Highly preferred pH is around pH 5, which corresponds to the skin pH. By pH of chitosan material it is meant herein the pH of a 1% chitosan solution (1 gram of chitosan material dissolved in 100 grams of distilled water) measured by pH-meter.

The cationic properties of the chitosan materials and thus their antimicrobial, absorbing ability and gelifying ability increase with their acidic character. However too high acidity is detrimental to skin safety. Thus it is highly preferred herein to use chitosan materials with a pH in the range of 4.5 to 5.5, thereby delivering the best compromise between odor control and fluid handling properties on one side and skin compatibility on the other side.

Particularly suitable aminopolysaccharides for use herein include aminopolysaccharide salts, especially chitosan salts. A variety of acids can be used for forming aminopolysaccharide salts like chitosan salts. Suitable acids for use are soluble in water or partially soluble in water, are sufficiently acidic to form the ammonium salt of the aminopolysaccharides and yet not sufficiently acidic to cause hydrolysis of the aminopolysaccharides, and are present in amount sufficient to protonate the reactive sites of the deacetylated aminopolysaccharide.

Preferred acids can be represented by the formula:

wherein n has a value of 1 or 2 or 3 and R represents a mono- or divalent organic radical composed of carbon, hydrogen and optionally at least one of oxygen, nitrogen and sulfur or R simply is a hydroxyl group. Preferred acids are the mono- and dicarboxylic acids composed of carbon, hydrogen, oxygen and nitrogen (also called herein after amino acids). Such acids are highly desired herein as they are biologically acceptable for use against or in proximity to the human body. Illustrative acids, in addition to those previously mentioned include, among others, citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, 2-pyrrolidone-5-carboylic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid and thioglycolic acid. Any aminopolysaccharide salts, especially chitosan salts formed from the reaction of the aminopolysaccharide with any of these acids are suitable for use herein.

Examples of chitosan salts formed with an inorganic acid include, but are not limited to, chitosan hydrochloride, chitosan hydrobromide, chitosan phosphate, chitosan sulphonate, chitosan chlorosulphonate, chitosan chloroacetate and mixtures thereof. Examples of chitosan salts formed with an organic acid include, but are not limited to, chitosan formate, chitosan acetate, chitosan lactate, chitosan glycolate, chitosan malonate, chitosan epoxysuccinate, chitosan benzoate, chitosan adipate, chitosan citrate, chitosan salicylate, chitosan propionate, chitosan nitrilotriacetate, chitosan itaconate, chitosan hydroxyacetate, chitosan butyrate, chitosan isobutyrate, chitosan acrylate, and mixtures thereof. It is also suitable to form a chitosan salt using a mixture of acids including, for example, both inorganic and organic acids.

Preferred aminopolysaccharide salts, and especially chitosan salts for use herein are those formed by the reaction of aminopolysaccharides with an amino acid. Amino acids are molecules containing both an acidic and amino functional group. The use of amino acids is highly preferred as those aminopolysaccharide amino salts have higher skin compatibility. Indeed most of the amino acids are naturally present on the skin and thus are non-irritating. Chitosan salts of pyrrolidone carboxylic acid are effective moisturizing agents and are non-irritating to skin. Such chitosan materials are suitable in case of accidental low rewetting occurrence and/or misuse of the articles.

Amino acids for use herein include both linear and/or cyclo amino acids. Examples of amino acids for use herein include, but are not limited to, alanine, valine, leucine, isoleucine, prolinephenylalanine, triptofane, metionine, glycine, serine, cysteine, tyrosine, asparagine, glutamine, aspartic acid, glutamic acid, lysine, arginine, istydine, hydroxyproline and the like. A particularly suitable example of cyclo amino acid is pyrrolidone carboxylic acid, which is a carboxylic acid of pyrrolidin-2-one as per following formula:

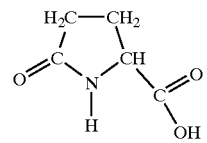

Reference is made to WO98/07618, which describes in details processes for the preparation of such aminopolysaccharide salts.

Other aminopolysaccharide materials suitable for use herein include modified aminopolysaccharides, especially modified chitosans.

Modified chitosans or chitins for use herein are any chitosan or chitin where the glucan chains carry pendant groups. Examples of such modified chitosans include carboxymethyl chitosan, methyl pyrrolidinone chitosan, glycol chitosan and the like. Methyl pyrrolidone chitosan is for instance described in U.S. Pat. No. 5,378,472, incorporated herein by reference. Water-soluble glycol chitosan and carboxymethyl chitosan are for instance described in WO 87/07618, incorporated herein by reference Particularly suitable modified chitosans for use herein include water-soluble covalently bonded chitosan derivatives or ionically bonded chitosan derivatives obtained by contacting salt of chitosan with electrophilic organic reagents. Such water-soluble chitosan derivatives are described in EP-A-737 692, which is herein incorporated by reference.

Suitable electrophilic organic reagents suitable for use for the preparation of chitosan derivatives contain from 2 to 18 carbon atoms or more per molecule and typically from 2 to 10 carbon atoms per molecule. In addition the electrophilic organic reagents contain groups, which are reactive, i.e. capable of forming a covalent bond with a nucleophile. Typical electrophilic organic reagents include, for example, ethylene oxide, propylene oxide, butylene oxide, glycidol, 3-chloro-1,2-propanediol, methyl chloride, ethyl chloride, isatoic anhydride, succinic anhydride, octenylsuccinic anhydride, acetic anhydride, gamma-butyrolactone, b-propiolactone, 1,3-propanesultone, acrylamide, glycidyltrimethyl ammonium chloride, glycidyldimethyl alkylammonium chloride such as lauryl, sodium chlorosulfonate, dimethyl sulfate, sodium chloroethanesulfonate, monochloroacetic acid, alkyl phenyl glycidyl ethers, glycidyl trimethoxysilanes, 1,2-epoxy dodecane. One preferred class of electrophilic organic reagent includes those electrophilic organic reagents, which contain an epoxide group, at least one acid group, preferably a diacid group and have from 3 to 18, preferably from 3 to 6 carbon atoms per molecule. Other preferred electrophilic organic reagents include cis-electrophilic organic reagents and transelectrophilic organic reagent, with cis-electrophilic organic reagents being especially preferred. The electrophilic organic reagent may react with either the free amine or the underivatized hydroxyl groups of the chitosan. It is known that the amine functionality of the chitosan is generally regarded as a stronger nucleophilic site than the hydroxyl groups. Consequently weaker electrophiles will tend to react more readily with the amine groups than with the hydroxyl groups of the chitosan.

Preferably an effective amount of electrophilic organic reagent is substituted onto the chitosan to achieve the desired properties of the chitosan derivative, namely its water-soluble properties. Typically the chitosan derivatives suitable for use herein (modified chitosan) have a MS of from 0.03 to 10 moles of the electrophilic organic reagent per mole of glucosamine monomer unit. The term molar substitution (MS), means the moles of electrophilic organic reagent substituted on the chitosan per mole of glucosamine monomer unit.

In addition further modified chitosan can be prepared which contain other substituent groups, such as hydroxalkyl ether group (e.g., hydroxyethyl or hydroxypropyl ether groups), carboxyalkyl ether groups (e.g., carboxymethyl group), amide groups (e.g., succinyl groups), ester groups (e.g., acetate groups) or amino groups (e.g., 3-(trimethylammonium chloride)-2-hydroxylpropyl or 3-(dimethyloctadecylammonium chloride)-2-hydroxpropyl ether groups) in addition to the electrophilic organic reagent groups. These other substituent groups may be introduced prior to or subsequent to the reaction with the electrophilic organic reagent, or introduced simultaneously by reaction of the chitosan salt with the electrophilic organic reagent and the other derivatizing reagent.

Typically such covalently bonded chitosan derivative might be obtainable by a process which includes the step of (a) dispersing a salt of chitosan (e.g., any one of those described herein before) in an effective amount of an aqueous caustic medium to form a neutralized chitosan containing free amine groups, (b) introducing an electrophilic organic reagent in the slurry and (c) maintaining the slurry at a temperature and time effective to promote the substitution of the electrophilic organic reagent onto the chitosan to form a covalently bonded chitosan derivative and the dissolution of the covalently bonded chitosan into the aqueous medium. The chitosan derivatives can be prepared in either salt form, i.e., ionically bonded, or in the covalently bonded form. Processes for the preparation of such chitosan derivatives are described in depth in EP-A-737 692, incorporated herein by reference.

Suitable chitosans are commercially available from numerous vendors. Exemplary of a commercially available chitosan materials are those available from for example the Vanson Company. The preferred chitosan salt for use herein is chitosan pyrrolidone carboxylate (also called chitosonium pyrrolidone carboxylate), which has a degree of deacetylation of more than 85%, a water solubility of 1% (1 gram is soluble in 100 grams of distilled water at 25° C. and one atmosphere), a pH of 4.5 and a viscosity between 100-300 cps. Chitosan pyrrolidone carboxylate is commercially available under the name Kytamer® PC from Amerchol Corporation.

Typically, the articles like disposable absorbent articles, comprise cationic polysaccharide or a mixture thereof at a level of from 0.5 $gm^{-2}$ to 500 $gm^{-2}$, preferably from 1 to 200 $gm^{-2}$, more preferably from 3 $gm^{-2}$ to 100 $gm^{-2}$ and most preferably from 4 $gm^{-2}$ to 50 $gm^{-2}$.

In a preferred embodiment herein the cationic polysaccharide and the silica are present in weight ratio from the cationic polysaccharide to the silica of from 0.1 to 50, preferably 0.5 to 30 and more preferably at a ratios around 1. Indeed it is within these ranges that optimum odor control and optimum fluid handling are obtained.

Optional Agents

The articles according to the present invention preferably further comprise other agents to further enhance the properties of such articles.

Optional Crosslinking Agents

A highly preferred optional agent is the presence of a crosslinking agent or a mixture thereof.

Suitable crosslinking agents for use herein are any organic compound having at least two functional groups or functionalities capable of reacting with active groups located on the aminopolysaccharides, typically chitosan materials. Examples of such active groups include, but are not limited to, carboxylic acid (—COOH), amino (—NH$_2$), or hydroxyl (—OH) groups. Examples of such suitable crosslinking agents include, but are not limited to, diamines, polyamines, diols, polyols, acids, polyoxides, dialdehydes, polyaldehydes, diepoxides and the like. Specifically, the crosslinking agents may be selected from the group consisting of glutaraldehyde, carboxymethyl cellulose, poly (ethylen glycol) diglycidal ether, and bis(polyoxyethylene bis(glycidyl ether)) and mixtures thereof.

Other suitable crosslinking agents are multibasic acids. Highly suitable multibasic acids for use herein include amino carboxylic acids, amino polycarboxylic acids, dicarboxylic acids and polycarboxylic acids. Examples of such multibasic acids useful as crosslinking agents herein include glutamic acid, aspartic acid, pyrophosphoric acid, adipic acid, butane tetracarboxylic acid, citric acid, glutaric acid, itaconic acid, malic acid, malonic acid, mesaconic acid, methylsuccinic acid, oxalic acid, o-phthalic acid, m-phthalic acid, p-phthalic acid, succinic acid, alpha tartaric acid and meso-tartaric acid. Preferably the crosslinking agent is selected from the group consisting of adipic acid, butane tetracarboxylic acid, citric acid, glutaric acid, itaconic acid, malic acid, succinic acid and mixtures thereof.

Other suitable crosslinking agents also include metal ions with at least two positive charges and which are effective to form coordination bonds with the cationic polysaccharide salts, namely the chitosan salts, such as $Cu^{2+}$, $Al^{3+}$, $Fe^{3+}$, $Ce^{3+}$, $Ce^{4+}$, $Ti^{4+}$, $Zr^{4+}$, and $Cr^{3+}$. Suitable metal ion crosslinking agents include those of the transition elements, which generally have vacant d-orbitals. Suitable metal ion crosslinking agents include $CuSO_4$, $ZrCl_4$, $FeCl_3$, $Ce(SO_4)_3$, and $Ce(NH_4)_4(SO_4)_4.2H_2O$, other well-known metal ion compounds and mixtures thereof. Such metal ion crosslinking agents, when used with a chitosan salt, are believed to form chelates with the chitosan salts.

Since the cations on the cationic polysaccharides, namely chitosan materials, are essential for the antimicrobial properties, fluid handling properties and gelification properties of said materials, it is preferred herein to not use a crosslinking agent reacting to the cations. Particularly suitable crosslinking agents herein are acids, especially dicarboxylic acids and polycarboxylic acids as described herein before, which esterify the hydroxyl groups of the cationic polysaccharides, like chitosan materials. The presence of such crosslinking agents, will not impair on the odor control properties and fluid handling properties of the cationic polysaccharides, namely chitosan materials, and may even improve such properties.

In the embodiment herein where crosslinked-cationic polysaccharides are used, a suitable amount of crosslinking agent is from 0.001 to 30 weight percent based on the total dry weight of the cationic polysaccharide (e.g., chitosan material) used to prepare the crosslinked-cationic polysaccharide, more specifically from 0.02 to 20 weight percent, more specifically from 0.05 to 10 weight percent and most preferably from 0.1 to 5 weight percent.

In a preferred embodiment herein the crosslinking agents used herein are those having at least two functional groups or functionalities capable of reacting with active groups located on the aminopolysaccharides, namely carboxylic acid (—COOH), amino (—NH$_2$), or hydroxyl (—OH) groups but also with active groups located on silica, namely hydroxyl (—OH) group.

Suitable crosslinking agents for forming crosslinked cationic polysaccharide-silica, namely crosslinked chitosan-silica are multibasic acids, typically those having at least two pKa (e.g., pKa$_1$ and pKa$_2$) that are both less than 5.5. Such acids may have more than two displaceable hydrogen atoms per molecule wherein the pKa$_m$ is less than 5.5, wherein m is an integer greater than 2. Highly suitable multibasic acids for use herein are amino carboxylic acids, amino polycarboxylic acids, dicarboxylic acids and polycarboxylic acids. Examples of such multibasic acids useful as crosslinking agents herein include aspartic acid, glutamic acid, pyrophosphoric acid, adipic acid, butane tetracarboxylic acid, citric acid, glutaric acid, itaconic acid, malic acid, malonic acid, mesaconic acid, methylsuccinic acid, oxalic acid, o-phthalic acid, m-phthalic acid, p-phthalic acid, succinic acid, alpha tartaric acid and meso-tartaric acid. Preferably the crosslinking agent is butane tetracarboxylic acid, citric acid, or a mixture thereof. Highly preferred is citric acid.

In the embodiment herein where crosslinked cationic polysaccharide-silica is used as the source of polysaccharide and silica according to the present invention, a suitable amount of crosslinking agent is from 0.05 to 70 weight percent based on the total dry weight of the cationic polysaccharide (e.g., chitosan material) together with silica used to prepare the crosslinked cationic polysaccharide-silica, more specifically from 0.1 to 50 weight percent, more specifically from 0.5 to 40 weight percent and most preferably from 1 to 35 weight percent.

Advantageously crosslinked silica-cationic polysaccharides, namely cross-linked silica-chitosan, are able to provide long lasting odor control properties and/or long lasting fluid handling properties. Indeed the use of crosslinked silica-chitosan in an absorbent article will deliver effective odor control properties and/or fluid handling towards bodily fluids and maintain them even upon prolonged wearing time of the article by the user, typically upon aging of the bodily fluid (typically menses) in the article and/or upon subsequent bodily fluid discharge in the article.

Without to be bound by any theory it is speculated that the crosslinked silica-cationic polysaccharide upon contact with bodily fluids like menses are slowly dissociated. For example in the case of polysaccharide-silica crosslinked by citric acid, the ester bonds between chitosan and citric acid as well as those between citric acid and silica are hydrolyzed upon subsequent bodily fluid discharge in the absorbent pad. This will result in release of the individual odor control actives in time sequence with the bodily fluid discharge and thus will maintain effective odor control properties upon prolonged use conditions of the absorbent article.

An additional benefit of the use of crosslinked silica-cationic polysaccharides is that powder leakage that may occur during the manufacturing, handling and/or use of the article is reduced as compared to using a mixture of silica and cationic polysaccharide powder. Advantageously by using one powder instead of two this result in ease of manufacturing process and hence in reduced manufacturing cost.

Method of producing the crosslinking polysaccharide-silica used in the present invention include any conventional crosslinking method known to those skilled in the art. One way is typically to mix a crosslinking agent with the cationic polysaccharide in distilled water. This can be done under heating, typically from 20° C. to 50° C., preferably around 40° C. for 10 minutes to 10 hours, typically around 1 hour. Then silica can be added to the obtained solution and kept under stirring for several hours (1 to 15 hours), typically one night. Then the so obtained solution is filtered and dried for 1 to 8 hours, typically 5 hours at 100° C.

In general, a crosslinking catalyst will not be needed, but may be beneficial, to assist in the crosslinking of the cationic polysaccharides salts of the present invention. Such crosslinking catalysts can be used in an amount of from 0.01 to 3 weight percent, suitable from 0.1 to 1 weight percent based on the total weight of cationic polysaccharides. A suitable crosslinking catalyst is sodium hypophosphite when citric acid is used as the crosslinking agent.

Optional Absorbent Gelling Materials

According to the present invention the articles comprise as an optional component an absorbent gelling material (sometimes referred to as "super-sorber").

Particularly preferred absorbent gelling materials for use herein are anionic absorbent gelling materials, i.e., absorbent gelling materials, which are predominantly negatively charged. These absorbent gelling materials can be any material having superabsorbent properties in which the functional groups are anionic, namely sulphonic groups, sulphate groups, phosphate groups or carboxyl groups. Preferably the functional groups are carboxyl groups. Particularly preferred anionic absorbent gelling materials for use herein are synthetic anionic absorbent gelling materials. Synthetic anionic absorbent gelling materials are preferred herein as they deliver higher odor and fluid absorption performance, this even under pressure, as compared to the absorption performance associated with natural anionic absorbent gelling materials like anionic polysaccharides when used in the same absorbent article.

Generally the functional groups are attached to a slightly cross-linked acrylic base polymer. For example the base polymer may be a polyacrylamide, polyvinyl alcohol, ethylene maleic anhydride copolymer, polyvinylether, polyvinyl sulphonic acid, polyacrylic acid, polyvinylpyrrolidone and polyvinylmorpholine. Copolymers of these monomers can also be used. Particular base polymers include cross-linked polyacrylates, hydrolyzed acrylonitrile grafted starch, starch polyacrylates and isobutylene maleic anhydride copolymers.

Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those, which, upon contact with fluids (i.e., liquids) such as water or body fluids, imbibe such fluids and thereby form hydrogels. These preferred absorbent gelling materials will generally comprise substantially water-insoluble, slightly cross-linked, partially neutralized, hydrogel-forming polymer materials prepared from polymerisable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example, (1) compounds having at least two polymerisable double bonds; (2) compounds having at least one polymerisable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1-0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, Reissue 32,649. The absorbent gelling materials which are especially useful in the absorbent articles herein are those which have an equilibrium extractable content in synthetic urine of no more than about 17%, preferably no more than about 10% by weight of the absorbent gelling material.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers, which have been neutralized with a salt-forming cation. Suitable salt-forming cations include alkali metal, ammonium, substituted ammonium and amines. This percentage of the total monomers utilized, which are neutralized acid group-containing monomers, is referred to as the "degree of neutralization". Typically, commercial absorbent gelling materials have a degree of neutralization somewhat from 25% to 90%.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reason of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use herein are absorbent gelling material s particles substantially all of which have a particle size of from about 30 microns to about 2 mm. "Particle Size" as used herein means the weighted average of the smallest dimension of the individual particles.

The amount of absorbent gelling material particles used in the article according to the present invention, especially disposable absorbent articles, will typically range from 5 $gm^{-2}$ to 250 $gm^{-2}$, preferably from 7 $gm^{-2}$ to 150 $gm^{-2}$, more preferably from 10 $gm^{-2}$ to 100 $gm^{-2}$.

Anionic absorbent gelling materials are suitably used on top of the cationic polysaccharide and silica herein as they contribute too to enhance the benefices of the present invention. Indeed the anionic absorbent gelling materials are believed due typically to their acidic properties to enhance the cationic properties of the cationic polysaccharides, thus their odor control properties and fluid handling properties.

Advantageously the addition of anionic absorbent gelling materials, namely synthetic anionic absorbent gelling materials as described herein (typically having a degree of neutralization of from 25% to 90%) on top of cationic polysaccharides, especially chitosan materials, in an absorbent article results in outstanding fluid absorption capacity not only towards water but especially towards electrolytes-containing solutions like menses.

Furthermore the use of anionic absorbent gelling materials, namely synthetic anionic absorbent gelling materials as described herein (typically having a degree of neutralization of from 25% to 90%) on top of cationic polysaccharides, especially chitosan materials, in an absorbent article, exhibits high gel strength during fluid absorption. Indeed this combination results in improved absorption capacity under load conditions, in decreased rewetting and wetting through and hence improved comfort.

Advantageously the presence of anionic synthetic absorbent gelling agents on top of the odor control system of the present invention (i.e., cationic polysaccharides and silica) results in optimum fluid absorption and optimum odor control of malodors typically associated with bodily fluids.

Optional pH Buffering Means

The articles herein may further comprise a pH buffering means or mixtures thereof, as an optional ingredient.

The presence of such a pH buffering means will contribute to maintain the odor control and fluid handling properties of the system herein. It is believed that the pH buffering means as described herein will help the silica in providing further enhanced cationic properties to the cationic polysaccharides, especially chitosan materials, and in maintaining these properties upon prolonged wearing time of the article of the present invention by the user. The presence of such pH buffering means is particularly suitable in the embodiment herein wherein silica and the cationic polysaccharides are used in non-crosslinked form.

By "pH buffering means", it is meant herein any compound which when added to a solution makes the solution to resist to a change in hydrogen ion concentration on addition of acid or alkali.

Preferred pH buffering means for use herein are acidic pH buffering means having a pH in the range of from 3.5 to 6.5, i.e., that the pH buffering means for use herein comprise a weak acid having its pKa (if only one) or at least one of its pKas in the range from 3.5 to 6.5, preferably from 4 to 6 and more preferably from 5 to 6, and its conjugated base.

$pK_a$ is defined according to the following equation:

$$pK_a = -\log K_a$$

where $K_a$ is the Dissociation Constant of the weak acid in water and corresponds to the following equation:

$$[A^-][H^{3O}]/[HA] = K_a$$

where HA is the acid and $A^-$ is the conjugated base.

By "conjugated base", it is meant herein the corresponding base ($A^-$) of the weak acid herein (HA). This conjugate base may be obtained by adding a source of alkalinity to the weak acid as defined herein. Suitable source of alkalinity suitable for use herein are the caustic alkalis such as sodium hydroxide, potassium hydroxide and/or lithium hydroxide and/or the alkali metal oxides such as sodium and/or potassium oxide. A preferred source of alkalinity is a caustic alkali, more preferably sodium hydroxide and/or potassium hydroxide. Alternatively the conjugate base may be commercially available per se and added directly to the weak acid herein.

Typically, according to the present invention the weak acid (HA) and its conjugate base ($A^-$) are in equilibrium according to the equation:

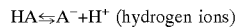

$HA \leftrightarrows A^- + H^+$ (hydrogen ions)

Typically the pH buffering means herein consists of a weak acid as defined herein and its conjugate base at a weight ratio of the weak acid to its conjugate base of preferably 0.1:1 to 10:1, more preferably 0.2:1 to 5:1. Highly preferred ratio of the weak acid to its conjugate base is 1 since this is the best combination to achieve optimum buffering capacity.

Preferably a given pH buffering means herein will be used to buffer mediums having a pH between pH=pKa−1 and pH=pKa+1 of each of its pKa. For example citric acid/citrate is particularly suitable to buffer mediums having a pH comprised between 3.74 and 5.74 (pKa 2=4.74). Bodily fluid discharges like perspiration, menses, and urine have an initial pH ranging between 5-6.5. Upon aging of the fluids in the absorbent article, the pH of the bodily fluids has the tendency to become more and more alkaline as a result of the degradative activity of microorganisms. The bodily fluids will be acidified and buffered by the acidic pH buffering means.

Suitable weak acids having at least one of their $pK_a$s of from 3.5 to 6.5 for use herein include citric acid ($pK_{a1}$=3.06, $pK_{a2}$=4.74), oxalic acid ($pK_{a2}$=4.19), tartaric acid ($pK_{a1}$=2.99, $pK_{a2}$=4.34), phtalic acid ($pK_{a1}$=2.89, $pK_{a2}$=5.41), acetic acid ($pK_a$=4.74), benzoic acid ($pK_a$=4.20), glutaric acid ($pk_{a1}$=4.34, pKa2=5.22), adipic acid ($pk_{a1}$=4.4, $pk_{a2}$=5.28) and/or carbonic acid ($pk_a$=3.8).

Particularly suitable pH buffering means for use herein are citric acid/sodium hydroxide, citric acid/sodium citrate, citric acid/potassium citrate, oxalic acid/sodium oxalate, tartaric acid/potassium hydrogen tartarate, oxalic acid/potassium tetra oxalate dihydrate, phtalic acid/potassium phtalate, phtalic acid/sodium phtalate acetic acid/sodium acetate, benzoic acid/sodium benzoate, glutaric acid/sodium glutarate, adipic acid/sodium adipate, carbonic acid/sodium carbonate or mixture thereof Preferred pH buffering means for use herein are citric acid/sodium citrate, citric acid/potassium citrate, citric acid/sodium hydroxide, oxalic acid/sodium oxalate, tartaric acid/potassium hydrogen tartarate, oxalic acid/potassium tetra oxalate dihydrate, and most preferred is citric acid/sodium citrate, citric acid/sodium hydroxide and/or citric acid/potassium citrate. Highly preferred pH buffering means for use herein is citric acid and sodium hydroxide.

Such acidic pH buffer system will contribute to the benefits of the present invention by further enhancing and maintaining the cationic properties of the chitosan materials herein, even upon aging of the bodily fluid, i.e., upon prolonged wearing time of an article by the user.

Typically, the articles like disposable absorbent articles comprise the acidic pH buffering means at a level of from 0.1 gm$^{-2}$ to 250 gm$^{-2}$, preferably from 1 to 150 gm$^{-2}$, more preferably from 10 gm$^{-2}$ to 100 gm$^{-2}$ and most preferably from 30 gm$^{-2}$ to 80 gm$^{-2}$ Optional Odor Controlling Agents Additional odor controlling agent or combinations thereof, known in the art for this purpose may be used herein too.

These agents can typically be classified according to the type of odor the agent is intended to combat. Alternatively, the odor controlling agents may be categorized with respect to the mechanism by which the malodor detection is reduced or prevented. For example, odor controlling agents which chemically react with malodorous compounds or with compounds which produce malodorous degradation products thereby generating compounds lacking odor or having an odor acceptable to consumers may also be utilized herein.

Suitable odor absorbent agents for use herein typically include activated carbons, clays, zeolites, diatomaceous earth and cyclodextrine. Such odor control agents and systems are disclosed in more details hereinafter and for example in EP-A-510 619, WO 91/12029, WO 91/11977, WO 91/12030, WO 81/01643 and WO 96/06589. Highly preferred additional odor controlling agent for use herein is zeolite.

In a preferred embodiment herein the absorbent article comprises zeolite on top of silica in a weight ratio of silica to zeolite in a range of from 1:5 to 5:1, preferably from 3:1 to 1:3 and most preferably about 1:1. This combination has been found to be particularly effective in terms of odor control over a broad range of malodorous compounds. Silica and zeolite have a complementary odor control properties towards various malodorous compounds, thereby resulting in further improved overall odor control reduction.

Suitable odor controlling agents also include chelating agents and may be selected from amino carboxylates such as for example ethylenediamine-tetracetate, as described for example in U.S. Pat. No. 4,356,190, amino phosphonates such as ethylenediaminetetrakis (methylene-phosphonates), polyfunctionally-substituted aromatic chelating agents as described in U.S. Pat. No. 3,812,044 and mixtures thereof. Without intending to be bound by theory it is believed that the benefit of these materials is in part due to their exceptional ability to remove iron, copper, calcium, magnesium and manganese ions present in the absorbed fluids and their degradation products by the formation of chelates.

Alternative odor control agents are ion exchange resins such as those described in U.S. Pat. No. 4,289,513 and U.S. Pat. No. 3,340,875.

Masking agents such as perfumes may also be used as odor control agents herein.

Typically, the articles like disposable absorbent articles may comprise the additional odor controlling agent or a mixture thereof at a level of from 0.5 $gm^{-2}$ to 600 $gm^{-2}$, preferably from 5 to 500 $gm^{-2}$, more preferably from 10 $gm^{-2}$ to 350 $gm^{-2}$ and most preferably from 20 $gm^{-2}$ to 200 $gm^{-2}$ The Absorbent Article Cationic polysaccharides and silica may be incorporated into the absorbent article by any of the methods disclosed in the art, for example layered on the core of the absorbent article or mixed within the fibers of the absorbent core.

Cationic polysaccharides, silica and optionally absorbent gelling materials are preferably incorporated between two layers of cellulose tissue. Optionally the system may be bonded between two cellulose tissue layers with, for example, a hot melt adhesive or any suitable bonding system, as described in WO 94/01069.

In one embodiment of the present invention the cationic polysaccharide, silica and/or optional absorbent gelling material and/or any other optional agent are incorporated in a layered structure in accordance with the disclosure of WO 94/01069 or Italian patent application number TO 93A 001028. TO 93A 001028 describes a layered structure substantially as described in WO 94/01069 with the exception that TO 93A 001028 comprises a much higher quantity of absorbent gelling material in the intermediate layer which is between the fibrous layers (120 $gm^{-2}$) that would be incorporated in the present invention as an optional ingredient. The intermediate layer comprises in particular a polyethylene powder as thermoplastic material, which is mixed with the cationic polysaccharide and silica and additional optional ingredients. The mixture is then heated such that the polyethylene melts and glues the laminate layers together. Adhesive lines are preferably also placed on the edges of the laminate to ensure that the edges of the laminate stick and any loose cationic polysaccharide, silica and optional absorbent gelling material and/or other optional agent present do not fall out of the laminate.

Alternatively, the polyethylene powder may be replaced by a conventional glue for instance those commercially available from ATO Findley under the name H20-31® to glue the laminate layers and/or components together. Advantageously this method step allows to avoid the heating step necessary when using polyethylene powder.

The cationic polysaccharides and silica may be distributed together or separately, homogeneously or non homogeneously, over the entire absorbent article or in at least one layer of the topsheet or in at least one layer of the backsheet, or in at least one layer of the core or any mixture thereof. The cationic polysaccharides and silica may be distributed homogeneously or non homogeneously on the whole surface of the desired layer or layers, or on one or several area of the surface layer/layers to which it is positioned (e.g. central area and/or surrounding area like the edges of a layer of the absorbent article) or mixtures thereof.

In some embodiments herein silica is positioned such that at least a portion of the fluid/exudate comes into contact with it before the cationic polysaccharide, preferably chitosan material. Typically silica is located towards the topsheet or located in the topsheet itself (preferably the secondary topsheet) and the cationic polysaccharide is located further away from the topsheet than silica. In one embodiment of the present invention, silica is positioned in at least one of the topsheet layers and the cationic polysaccharide; typically chitosan material is positioned in the core. In another embodiment herein silica is located in the core and the cationic polysaccharide is located further away in the core towards the backsheet or in the backsheet itself (preferably the secondary backsheet).

In a preferred embodiment herein, wherein an absorbent gelling material is present, the absorbent gelling material and silica are positioned such that at least a portion of the bodily fluid/exudate comes into contact with said absorbent gelling material and silica before the cationic polysaccharide. In a highly preferred embodiment herein the absorbent gelling material and silica are located in the core and the cationic polysaccharide, typically chitosan material, is located further away from the topsheet than the absorbent gelling material and silica. For example when a laminate is used as the core of the absorbent article, the absorbent gelling material and silica may be homogeneously mixed and dispersed between the two layers of the laminate, and the cationic polysaccharide may be applied on the lower layer of the laminate (the layer directed towards the backsheet), on either side thereof. Such executions may be obtained by spraying onto the surface of the layer a cationic polysaccharide-containing solution. Such executions are particularly beneficial for combining optimum odor control properties with optimum fluid handling, i.e., optimum odor and fluid absorption and retention without any leakage through or rewetting occurrence. The cationic polysaccharide due to its gelifying properties will have the tendency to form a so-called impermeable layer towards the backsheet thereby preventing any leakage through.

In other embodiments the cationic polysaccharides and silica may be located randomly together in various layers, i.e., that the total amount of cationic polysaccharides and silica is distributed in the topsheet layer and the core.

The cationic polysaccharides and silica as well as the optional absorbent gelling material if present may be incorporated as a powder, a granulate or can be sprayed in the form of for example a polysaccharide-containing solution and/or silica-containing solution within the absorbent article. When used in a granulate or particulate form the cationic polysaccharides (e.g., chitosan material) and silica as well as the optional absorbent gelling material may be granulated separately and then mixed together or granulated together.

Suitable disposable absorbent articles according to the present invention include those described as follows:

Absorbent Core

According to the present invention, the absorbent can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent may have any thickness depending on the end use envisioned.

a Primary/Secondary Fluid Distribution Layer

One optional component of the absorbent according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer. The fluid storage layer can comprise cationic polysaccharides (together with silica) and optional usual absorbent materials. It preferably comprises the cationic polysaccharides and optional absorbent gelling materials in combination with suitable carriers.

Suitable carriers include materials, which are conventionally utilized in absorbent structures such as natural, modified or synthetic fibers, particularly modified or non-modified cellulose fibers, in the form of fluff and/or tissues. Most preferred are tissue or tissue laminates in the context of sanitary napkins and panty liners.

An embodiment of the absorbent structure made according to the present invention may comprise multiple layers comprises a double layer tissue laminate formed by folding the tissue onto itself These layers can be joined to each other for example by adhesive or by mechanical interlocking or by hydrogen bridge bands. Cationic polysaccharides (together with silica) and optional absorbent gelling materials can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the cationic polysaccharides and optional absorbent gelling materials are dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing cationic polysaccharides and optionally absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

The Topsheet

According to the present invention the absorbent article comprises as an essential component a topsheet. The topsheet may comprise a single layer or a multiplicity of layers. In a preferred embodiment the topsheet comprises a first layer, which provides the user-facing surface of the topsheet and a second layer (secondary topsheet) between the first layer and the absorbent structure/core.

The topsheet as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as woven and non-woven fabrics and films. In a preferred embodiment of the present invention at least one of the layers, preferably the upper layer, of the topsheet comprises a hydrophobic, liquid permeable apertured polymeric film. Preferably, the upper layer is provided by a film material having apertures, which are provided to facilitate liquid transport from the wearer-facing surface towards the absorbent structure. Such apertured polymeric topsheet further participates to the odor control benefit. If present the lower layer preferably comprises a non-woven layer, an apertured formed film or an air laid tissue.

The Backsheet

The backsheet primarily prevents the extrudes absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions. In a preferred embodiment the backsheet comprises a first layer, which provides the garment-facing surface of the backsheet and a second layer (secondary backsheet) between the first layer and the absorbent structure/core.

The backsheet typically extends across the whole of the absorbent structure and can extend into and form part of or all of the preferred side flaps, side wrapping elements or wings.

The backsheet can comprise a woven or nonwoven material, polymeric films such as thermoplastic films of polyethylene or polypropylene, or composite materials such as a film-coated nonwoven material. Preferably, the backsheet is a polyethylene film typically having a thickness of from about 0.012 mm (0.5 mil) to about 0.051 mm (2.0 mil).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matt finished to provide a more cloth like appearance. Further, the backsheet can permit vapors to escape from the absorbent structure, i.e. be breathable, while still preventing exudates from passing through the backsheet. Also breathable backsheets comprising several layers, e.g. film plus non-woven structures, can be used. Breathable may be preferred herein as they contribute to further improve the odor control benefit associated with the present invention. Even more preferred herein the disposable absorbent articles have both a breathable backsheet and an apertured polymeric film topsheet for further increasing the odor control performance of the articles.

Odor Control Test

The odor reduction is measured by for example an in vitro sniff test. In vitro sniff test consists in analyzing by expert graders the odor associated with articles comprising the ingredients to be tested (including references articles) when contacted with an odorous components-containing solution.

The expert graders express their judgment about (un)pleasantness of the odor using a (un)pleasantness scale, typically from −10 (highest level of unpleasantness) to 5 (most pleasant). With this procedure, each grader compares MU (Unpleasantness) in the test session. The relative MU odor values from different products are assigned numbers. For example, in a test session, a sample that is perceived to be twice as strong as another is assigned twice as large a number. One that is perceived to be one-tenth as strong as another is assigned a number one-tenth as large, etc. In each test session, zero is used to designate neutral hedonicity, and + and − numbers are assigned in ratio proportion to the relative pleasantness and unpleasantness of the odor.

Surprisingly in vitro in-house sniff tests conducted by using an odorous components-containing solution reproducing the essential malodorous characteristics of menses showed synergistic odor reduction when comparing chitosan (e.g. chitosonium pyrrolidone carboxylate (Kytamer®) together with silica gel 123®, available from grace GmbH to each of these ingredients taken alone at the same total level of active. Indeed the % of unpleasantness reduction obtained for the mixture was higher than the % of unpleasantness reduction obtained for each of the two ingredients used alone at the same total level of active. The Unpleasantness values, for each sample, were obtained as a mean of at least 15 observations (3 products, 5 graders). These results were statistically significant.

Alternatively the odor reduction can also be measured with in vivo sniff tests as described in patent applications, EP-A-811387 or WO 97/46191, herein incorporated by reference.

The present invention is further illustrated by the following examples.

EXAMPLES

Example A

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper, which covers the external adhesive layer. The side of the absorbent fibrous core was then exposed by slightly shifting the water impermeable plastic bottom layer and subsequently, the fibrous core was split into two halves, each having approximately the same thickness, along a plane, which is parallel to the plane of the pad itself Chitosan material and silica were homogeneously distributed between the two fibrous layers.

The water impermeable inner backsheet was then put back into its original position and the wrap around perforated coverstock was sealed along the cut by means of e.g. a double-sided adhesive tape.

The chitosan powder material used was 0.3 g of chitosonium pyrrolidone carboxylate, commercially available from Amerchol Corporation, Edison, N.J. under the name Kytamer® PC.

Silica used was 0.3 g of Silica gel 123® or Syloblanc 82® available from Grace GmbH.

Example B

Other pads were prepared by following the method in Example A except that a pH buffering means was added on top of the chitosan material.

Accordingly a chitosan and pH buffering-containing solution was prepared by mixing 2 g of chitosan material together with 0.2 g a buffering pH means into 100 g of distilled water. The solution was stirred overnight at room temperature (25° C.). 10 g of the so obtained solution was sprayed onto the lower halve fibrous layer. This fibrous layer was then dried overnight at 40° C. in an oven. Silica was homogeneously distributed between the two fibrous layers. Then the two fibrous layers were joined together to reconstitute the absorbent core.

The chitosan powder material used was chitosonium pyrrolidone carboxylate, commercially available from Amerchol Corporation, Edison, N.J. under the name Kytamer® PC.

The pH buffering means used was citric acid/sodium hydroxide solution (pH 5) at a weight ratio 1:1, commercially available from Aldrich under the trade name Fixanal®.

Silica used was 0.2 g of Silica gel 123® or Syloblanc 82® available from Grace GmbH.

Example C

Other pads were prepared by following the method in Example A except that zeolite was added on top of silica and chitosan material. These three ingredients were homogeneously distributed between the two fibrous layers before reconstituting the pads Silica used was 0.2 g of Silica gel 123® or Syloblanc 82® available from Grace GmbH. Zeolite used was 0.4 g of Zeolite A, Wessalith C S, available from Degussa A G. The chitosan powder material used was 0.2 g of chitosonium pyrrolidone carboxylate, commercially available from Amerchol Corporation, Edison, N.J. under the name Kytamer® PC.

Example D

Other pads were prepared by following the method of Example A, except that instead of using a mixture of chitosan and silica individual powder, a crosslinked chitosan-silica powder was used. Indeed this powder was homogeneously distributed between the two fibrous layers before reconstituting the pads.

The crosslinked chitosan-silica powder was prepared as follows: 1 gram of chitosan was mixed together with 0.5 g of citric acid in 100 ml of distilled water. This solution was heated at 40° C. for one hour. Then 1 gram of silica was added to the previous solution and kept under stirring at room temperature (25° C.) for one night (10-12 hours). The so obtained solution was filtered using a paper filter (e.g., Circles 597® commercially available from Schleicher & Schuell Dassel, Germany) and dried at 100° C. for 5 hours to obtain a powder of crosslinked chitosan-silica. Citric acid is commercially available from Fluka. The chitosan powder material used was chitosonium pyrrolidone carboxylate, commercially available from Amerchol Corporation, Edison, N.J. under the name Kytamer® PC. Silica used was Silica gel 123® or Syloblanc 82® available from Grace GmbH.

0.5 g of crosslinked chitosan-silica powder was homogeneously distributed between the two fibrous layers. Then the tow fibrous layers were joined together to reconstitute the absorbent core.

Example E

Other pads were prepared by following the method in respectively Examples A, B, C and D, except that an absorbent gelling material (AGM) was homogeneously distributed between the two fibrous layers on top of the ingredients as described in Examples A, B, C and D before reconstituting the pads.

The AGM used was 0.3 g of cross-linked sodium polyacrylate XZ 9589001, available from Dow Chemicals.

Example F

Other pads were prepared by following the method in Example A except that after having split the fibrous core into two halves, an absorbent gelling material (AGM) and silica were respectively homogeneously distributed onto the upper halve fibrous layer (i.e. the fibrous layer halve intended to be closer to the topsheet) and chitosan material was homogeneously distributed onto the lower halve fibrous layer (i.e., the one intended to be closer to the backsheet of the pad once reconstituted). Then a layer of air laid tissue (19 mm*70 mm of low basis weight) available from Fripa under the code/name NCB Tissue HWS was positioned between the two halve fibrous layers which are then joined together to reconstitute the absorbent core. The presence of the air laid tissue between the two fibrous layers avoids direct contact between AGM and silica on one side and chitosan material on the other side.

AGM used was 0.3 g of cross-linked sodium polyacrylate, commercially available from Dow Chemicals (code:XZ 9589001).

Chitosan material used was 0.3 g of chitosonium pyrrolidone carboxylate, commercially available from Amerchol Corporation, Edison, N.J. under the name Kytamer® PC.

Silica used was 0.2 g of Silica gel 123® or Syloblanc 82® available from Grace GmbH.

Example G

Other pads were prepared by following the method in Example A except that after having split the fibrous core into two halves, a chitosan-containing solution was prepared and sprayed onto the inner lower halve fibrous layer (i.e., the one intended to be closer to the backsheet of the pad once reconstituted). By 'inner' it is meant onto the side to be in close proximity to AGM and silica, which were homogeneously distributed between the two fibrous layers before to reconstitute the pads.

AGM used was 0.3 g of cross-linked sodium polyacrylate, commercially available from Dow Chemicals (code:XZ 9589001). Silica used was 0.2 g of Silica gel 123® or Syloblanc 82® available from Grace GmbH.

Chitosan material used was 0.3 g of chitosonium pyrrolidone carboxylate, commercially available from Amerchol Corporation, Edison, N.J. under the name Kytamer® PC.

The chitosan-containing solution was prepared by mixing 2 g of chitosan material into 100 g of distilled water. The solution was stirred overnight at room temperature (25° C.). 10 g of the so obtained solution was sprayed onto the lower halve fibrous layer. This fibrous layer was then dried overnight at 40° C. in an oven. Silica and AGM were homogeneously distributed between the two fibrous layers. Then the tow fibrous layers were joined together to reconstitute the absorbent core.

Example H

The feminine pantiliner used in the following examples is a modified panty liner based on Always "Alldays Duo Ative" manufactured by Procter & Gamble, Germany. The topsheet is a film/non woven composite {film supplier code BPC 5105 CPM BP Chemical Germany, non-woven supplier code ARBO TB/BI Mequinenza Spain}. The core material is a tissue laminate (13.2 cm×4.0 cm) composed of a 2 layers of air laid tissue of 55 g/m$^2$ basis weight {available from Unikay Italy under the supplier code Unikay 303 LF}. Between the two tissue layers the laminate contains chitosan material together with silica.

The backsheet comprises two layers a first layer and a second layer. The first layer is in contact with the absorbent tissue and the second layer. The second layer is in contact with the first layer and the undergarment of the wearer. The first layer is a formed apertured film (CPT) made of Low Density PE {supplied by Tredegar Film Products B. V. Holland under the manufacturing code X-1522}. The second layer is composed of a nonwoven laminate {13MB/16SB manufactured by Corovin GmbH in Germany under the trade name MD 2005}. The nonwoven laminate is composed of 16 g/m$^2$ spun bond and 13 g/m$^2$ meltblown. Each backsheet layer is joined over the full surface by an extensively overlapped spiral glue application at a basis weight of approximately 8 g/m$^2$. The glue utilized for attachment of both backsheet layers was supplied by SAVARE' SpA. Italy (under the material code PM17).

The chitosan material used was 0.2 g of chitosonium pyrrolidone carboxylate, commercially available from Amerchol Corporation, Edison, N.J. under the name Kytamer® PC. Silica used was 0.2 g of Silica gel 123 or Syloblanc 82 available from Grace GmbH.

Example I

Other panty liners can be made starting from the ones exemplified in Example H above except that AGM is incorporated on top of the chitosan material and silica. Indeed the 3 powders were homogeneously distributed between the two layers of the laminate. AGM used was 0.3 g of cross-linked sodium polyacrylate, commercially available from Dow Chemicals (code:XZ 9589001).

All the above-exemplified absorbent articles delivered outstanding odor control benefits and fluid handling benefits when coming into contact with bodily fluids like menses.

What is claimed is:

1. A disposable absorbent article comprising a liquid pervious topsheet, a backsheet; an absorbent core comprising a crosslinked silica cationic polysaccharide; said core intermediate to said backsheet and said topsheet.

2. An article according to claim 1 wherein said article is a disposable absorbent article selected from the group consisting of a sanitary napkin, a pantiliner, a tampon, a diaper, an incontinent pad, a breast pad, a perspiration pad, an interlabial pad or a body cleaning article.

3. An article according to claim 1 wherein the cationic polysaccharide is an aminopolysaccharide selected from the group consisting of chitosan, chitosan salt, modified chitosan, crosslinked chitosan and a mixture thereof.

4. An article according to claim 1 wherein the cationic polysaccharide is a chitosan material having a degree of deacetylation of more than 75%, preferably from 80% to about 100%, even more preferably from about 90% to about 100% and most preferably from about 95% to about 100%.

5. An article according to claim 1 wherein the cationic polysaccharide is a chitosan salt, a chitosan salt of citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid, thioglycolic acid, alanine, valine, leucine, isoleucine, prolinephenylalanine, triptofane, metionine, glycine, serine, cysteine, tyrosine, asparagine, glutamine, lysine, arginine, istydine, hydroxyproline, pyrrolidone carboxylic acid, chitosonium pyrrolidone carboxylate and mixtures thereof.

6. An article according to claim 1 which comprises from about 0.5 $gm^{-2}$ to about 500 $gm^{-2}$ of a cationic polysaccharide or a mixture thereof.

7. An article according claim 1 which comprises from about 5 to about 300 $gm^{-2}$ of silica based on 100% purity or a mixture thereof.

8. An article according to claim 1 further comprising an additional odor controlling agent selected from the group consisting of zeolites, diatomaceous earth, carbons, starches, cyclodextrin and derivatives thereof, kieselguhr, clays, ion exchange resins, chelating agents and combination thereof.

9. An article according to claim 8 which comprises from about 0.5 to about 600 $gm^{-2}$ of the additional odor controlling agent or a mixture thereof.

10. An article according to claim 1 further comprising a pH buffering means which has a pH in the range of from about 3.5 to about 6.5 and comprises a weak acid having its pKa (if only one) or at least one of its pKas in the range from about 3.5 to about 6.5 and its conjugated base.

11. An article according to claim 10 wherein the pH buffering means is citric acid/sodium citrate, citric acid/sodium hydroxide and/or citric acid/potassium citrate.

12. An article according to claim 11 wherein the acidic pH buffering means at a level of from about 0.1 $gm^{-2}$ to about 250 $gm^{-2}$.

13. An article according to claim 1 further comprising an absorbent gelling material.

14. An article according to claim 13, wherein the absorbent gelling material is present at a level from about 5 $gm^{-2}$ to about 250 $gm^{-2}$.

15. An article according to claim 1 wherein the crosslinking agent used is any crosslinking agent having at least two functional groups or functionalities capable of reacting simultaneously with at least one active group located on the cationic polysaccharide as well as with at least one active group located on silicate, preferably the crosslinking agent is a multibasic acid, typically a dicarboxylic acid, polycarboxylic acid, aminocarboxylic acid, aminopolycarboxylic acid, or a mixture thereof, more preferably is aspartic acid, glutamic acid, pyrophosphoric acid, adipic acid, butane tetracarboxylic acid, citric acid, glutaric acid, itaconic acid, malic acid, malonic acid, mesaconic acid, methylsuccinic acid, oxalic acid, o-phthalic acid, m-phthalic acid, p-phthalic acid, succinic acid, alpha taxtaric acid, meso-tartaric acid or a mixture thereof.

* * * * *